United States Patent
Wendell

[11] Patent Number: 5,100,379
[45] Date of Patent: Mar. 31, 1992

[54] MICROCATHETER HAVING IMPROVED TENSILE STRENGTH

[75] Inventor: Amy M. Wendell, Franklin, Mass.

[73] Assignee: The Kendall Company, Mansfield, Mass.

[21] Appl. No.: 615,943

[22] Filed: Nov. 19, 1990

[51] Int. Cl.$^5$ .............................................. A61M 31/00
[52] U.S. Cl. ..................................... 604/51; 604/158; 604/282; 260/209.5
[58] Field of Search .................. 264/209.5, 210.7; 604/264, 158, 280, 282, 51, 52, 53

[56] References Cited

U.S. PATENT DOCUMENTS

| | | | |
|---|---|---|---|
| 3,630,824 | 12/1971 | Rollig | 264/210.7 X |
| 3,725,519 | 4/1973 | Seifried et al. | 264/210.7 X |
| 4,376,746 | 3/1983 | Ward et al. | 264/209.5 X |
| 4,451,306 | 5/1984 | Verne | 264/210.5 X |
| 4,698,196 | 10/1987 | Fabian | 264/565 |
| 4,886,634 | 12/1989 | Strutzel et al. | 264/560 |
| 4,917,670 | 4/1990 | Hurley et al. | 604/51 |
| 4,973,312 | 11/1990 | Andrew | 604/158 |

FOREIGN PATENT DOCUMENTS 8909079  10/1989  PCT Int'l Appl. .................. 604/282

*Primary Examiner*—John D. Yasko
*Assistant Examiner*—Adam J. Cermak
*Attorney, Agent, or Firm*—Alvin Isaacs

[57] ABSTRACT

A wireless polymeric microcatheter having improved tensile strength; and the process for making same.

19 Claims, No Drawings

MICROCATHETER HAVING IMPROVED TENSILE STRENGTH

BACKGROUND OF THE INVENTION

The present invention relates in general to microcatheters and more specifically to catheters intended for administering spinal anesthesia which possess markedly improved tensile strength.

Microcatheters are catheters having an external diameter less than 0.022 inches or 0.559 mm and an internal diameter greater than 0.004 inches or 0.102 mm. Such catheters are predominantly used in the vertebrae region to administer continuous spinal, epidural and caudal anesthesia. The anatomical and physiological nuances encountered in the vertebrae column in general mandate a flexible, small diameter catheter on the one hand and on the other hand, one with structural integrity, particularly tensile strength to enable threading through a spinal needle and to prevent catheter breakage upon removal of the catheter from the spinal column.

As an example of such a microcatheter, mention may be made of the "CoSPAN" (trademark of The Kendall Company, assignee of the instant invention) for a 28 gauge nylon catheter which can be inserted with a 22 gauge needle. The catheter can dispense 1 ml of fluid in less than a minute as well as being employed to aspirate fluid. It possesses a mean breaking force of on the order of about 1.8 pounds force.

As used herein, the term "breaking force" is the maximum force in pounds which the specimen can bear before breaking. Tensile strength, then, is the breaking force divided by the cross-sectional area, which may then be represented by the formula:

$$TS = \frac{BF}{X}$$

where TS=tensile strength; BF=breaking force; and X=cross-sectional area

As a further example of commercially available microcatheters for spinal anesthesia, mention may be made of the 28 gauge polyurethane microcatheter made by Preferred Medical which possesses a tensile strength comparable to that of the aforementioned CoSPAN microcatheter.

While not intended to represent an exhaustive survey of the patent literature, the following patents representing a cursory search may nevertheless be taken as illustrative.

U.S. Pat. No. 3,780,733 teaches (1) first partially inserting a 15 gauge needle into the dural space; (2) guiding a 25 gauge needle coupled to a 20 gauge catheter through the 15 gauge needle lumen into the subarachnoid space with the use of stylet inserted in the catheter.

While the actual puncture created in the subarachnoid space with the 25 gauge needle is small, disadvantages exist. For one, the needle may discouple from the, catheter and become dislodged in the spinal column. Secondly, the technique disadvantageously requires that the metal needle be maintained in the subarachnoid space throughout the surgery thereby creating possible injuries due to physical movement of the metal needle. Thirdly, the metal guiding stylet may cause impact trauma during insertion.

U.S. Pat. No. 4,917,670 teaches a polymeric microcatheter having an external diameter less than about 0.0120 inch (0.305 mm), so that it will fit through a thin wall 24 to 26 gauge spinal needle, with a reinforcing stylet inserted or affixed therein. While this invention alleviates the discoupling risk and prolonged insertion of the metal needle for the duration of the surgery, it still requires the use of a metal stylet.

Lastly U.S. Pat. No. 3,634,924 claims, "[T]he method of making a balloon catheter comprising providing a catheter tube of a thermoplastic material having a memory characteristic and containing a balloon inflation lumen, applying heat to an end portion of said tube sufficient to soften said material, drawing out and elongating said softened portion to shrink its diameter, applying a pair of rigid ferrules over said shrunken portion, applying heat to said shrunken portion to reexpand its diameter and lock said ferrules on said tube, forming a balloon inflation opening in said material communicating with said lumen, applying a sleeve of elastic balloon material over said reexpanded portion, and binding said balloon material to said ferrules."

Spinal anesthesia is a commonly employed anesthesia for almost any type of major procedure below the level of the diaphragm. Spinal anesthesia involves blockage of the nerve roots and spinal cord to prevent transmission of nerve impulses. Saddle block anesthesia or low spinal anesthesia is similar to spinal anesthesia except that the anesthetic agent is injected between the 3rd and 4th lumbar space as opposed to the 2nd and 3rd lumbar space in spinal anesthesia and, therefore, mainly produces anesthesia in the perineal area. Caudal block anesthesia in contract produces more extensive anesthesia than saddle block, namely from the umbilicus to the toes.

Spinal anesthesia involves a lumbar puncture and spinal tap. The lumbar puncture is performed by an anesthesiologist between the second and third lumbar vertebrae.

The procedure is begun by prepping the patient's skin surrounding the puncture site with an antiseptic and draping the patient with a sterile towel. Next a local anesthetic is administered to the site to produce a local nerve block. Once the area is anesthetized, a spinal needle is inserted and a local anesthetic agent is injected through the spinal needle into the subarachnoid space between the pia mater and the arachnoid membrane into the spinal fluid.

If the procedure is predicted to take longer than 3–4 hours, which is the time of the longest acting single dose anesthetic agent, a continuous spinal anesthesia is preferred to avoid repeated lumbar punctures. A continuous spinal anesthesia involves the insertion of a semi-rigid catheter threaded through the spinal needle and into the subarachnoid space. This procedure advantageously allows for intermittent anesthetic administration since the catheter remains in place throughout the operation.

In general, the microcatheters of the prior art tend to possess an undesirably low tensile strength. While the tensile strength may be increased to a point by selection of the polymeric material employed in its synthesis, e.g. the nylon from which the CoSPAN is made, there is still a need in the art to increase the tensile strength of these thin walled catheters still further. Accordingly, the microcatheters of the prior art either utilize a reinforcing metal wire embedded in the polymeric catheter wall to enhance tensile strength or, if wireless, the tensile strength is sufficiently low to present the inherent danger of breakage on removal. The consequences of having catheter parts left in the spinal column are obviously disastrous.

As heretofore mentioned, the nylon material utilized in the manufacture of the CoSPAN spinal catheter will provide a 28 gauge catheter having mean breaking force slightly in excess of 1.5 pounds. While this tensile strength is entirely satisfactory in most spinal anesthesia procedures, breakage can and will still occur, mainly due to human error.

For example, breakage is often the result of an inadvertent attempt to withdraw the catheter backward against the needle bevel. Strict avoidance of such back-pulling should minimize the rare incidence of this complication. Another cause of breakage is the compressive forces which retain the catheter (which is referred to as the "Laminer Pincer"). This cause of breakage can be minimized by flexing the patient's spine while the catheter is being gently removed. Knotting of the catheter, which may also contribute to catheter breakage, can be minimized by properly inserting no more than 2 to 4 cm of catheter into the subarachnoid space.

In those infrequent instances where breakage of the CoSPAN catheter does occur, the patient must first be informed and reassured. X-rays may be used to locate the segment of broken catheter, and if it is just below the skin line, it can be removed under local anesthesia.

On the other hand, while the use of a reinforcing wire embedded in the catheter wall may increase the tensile strength to a level preventing breakage on removal, the presence of this reinforcing wire also presents inherent danger to the patient. For example, if the catheter having a reinforcing wire is bent on insertion, it stays bent, thereby inhibiting the flexibility needed for insertion. If it is kinked, it will stay kinked, thus lowering the flow rate for the spinal anesthesia or other liquid to be administered. Further, it the wire causes the catheter to be relatively stiff, it may track straight ahead on insertion and possibly embed itself in the tissue wall of the dura mater or, even worse, puncture it to cause a leak of spinal fluid, nerve damage, or both.

Accordingly, the task of this invention, simply stated, is to provide microcatheters for medical procedures such as continuous spinal anesthesia which are characterized by a substantially greater breaking force sufficient to materially inhibit if not preclude breakage on removal, which microcatheters are accordingly wireless and thereby obviate the dangers inherent in the use of reinforcing wires.

BRIEF DESCRIPTION OF THE INVENTION

In accordance with the present invention, this task is solved in an elegant manner by a novel process of manufacture wherein a tubing comprising a polymeric material which can be elongated by stretching is elongated to provide a microcatheter of reduced diameter and which, due to the molecular orientation by stretching, possesses a markedly superior breaking force as compared to a microcatheter of the same diameter prepared by conventional extrusion techniques.

The present invention contemplates providing microcatheters ranging from 24 to 32 gauge, with a 28 gauge microcatheter having a tensile strength of at least 2.5 pounds force with forces on the order of 3.0 or greater being particularly preferred.

DETAILED DESCRIPTION OF THE INVENTION

Continuous spinal anesthesia is widely recognized as an advantageous method for administering regional spinal anesthesia for a wide array of operations below the diaphragm. Continuous spinal anesthesia is administered in the following fashion.

The patient is prepped with an antiseptic solution in the area surrounding the 2nd and 4th lumbar vertebrae. The area is then draped off to create a sterile field. A local anesthetic is next injected into the actual puncture site to create a local nerve block. Once the area is anesthetized, a spinal needle is inserted between the vertebrae until the tip of the needle penetrates the subarachnoid space. Next, a microcatheter is inserted through the needle, until the tip of the catheter projects beyond the tip of the spinal needle and enters into the subarachnoid space. The needle is then removed leaving the catheter undisturbed in place. The anesthesiologist may then administer the anesthetic agent as needed. The anesthetic agent may be administered by any number of infusion techniques through a catheter adaptor portal, most commonly by the use of a syringe.

As heretofore mentioned, the task of the present invention is to provide microcatheters of greatly increased breaking force so as to materially inhibit if not completely preclude the danger of breakage on removal, which microcatheters are wireless so as to obviate the aforementioned dangers in the use for administering spinal anesthesia of catheters having a reinforcing wire embedded in the catheter wall.

Other objects of the invention will in part be obvious and will in part appear hereinafter in the following detailed description of the invention.

As used throughout the specification and appended claims, the term "microcatheter" denotes a catheter whose size ranges from 32 gauge (outer diameter of about 0.009 inch or 0.229 mm) to as large as 24 gauge (outer diameter of about 0.022 inch or 0.559 mm). Preferred are 28 gauge microcatheters having an outer diameter (OD) of about 0.0145 in. (0.368 mm) and an inner diameter (ID) of about 0.0075 in. (0.191 mm).

In accordance with the present invention, microcatheters having the requisite breaking force are prepared by stretching or elongating a tubular article of greater diameter comprising a medical grade polymeric material whereby to molecularly orient the tubular walls while reducing the OD to the desired microcatheter size. The thus elongated and molecularly oriented catheter tube possesses essentially the same breaking force as did the initial tube prior to stretching.

In general, the polymeric material to be employed to prepare the initial tubing (which is the starting point of the present invention) may be any material which can be elongated to reduce the OD of the tubing to the desired microcatheter OD. The selection of such materials will be apparent to those skilled in the art in the light of the present disclosure and per se comprises no part of this invention. However, as alluded to previously, some polymeric materials have greater tensile strength than others. For example, the following comparative tensile strengths (measured in pounds per square inch) were reported in "A Report on the CoSPAN TM Catheter for Continuous Spinal Anesthesia" (1989), Kendall Healthcare Products Company:

| Material | Tensile Strength |
| --- | --- |
| Polyvinyl chloride | 700 |
| FEP "Teflon" | 3000–4000 |
| Urethane (poly-ether types) | 6500 |
| Kendall nylon | 10000 |

For this reason, elongatable materials such as the nylons (a family of high-strength, resilient, synthetic materials, the long-chain molecule of which contains the recurring amide group CONH) and polyurethane are preferred, nylons of the class known in the art as Nylon 11 being particularly preferred. Other useful starting materials, e.g. polyolefins such as polyethylene and polypropylene will also be suggested to the skilled worker.

In the preferred embodiments of this invention, the selected polymeric material will be capable of at least 200% elongation, most preferably on the order of 300% and the tubing will be molecularly oriented by stretching sufficient to provide at least a 50% increase in a tensile strength and, most preferably, at least a 70% increase.

The microcatheters of this invention having the requisite size and tensile strength may be made in the following manner.

Medical grade polymeric materials preferably having at least 200% elongation are extruded to form catheter tubing using commonly known in the art extrusion apparatus and techniques. The extruded tubing is then stretched to reduce the diameter to the desired size microcatheter. The stretching may be performed on hot or cold extruded polymeric material, using precut segments of tubing or uncut rolls of tubing. The stretching itself may be accomplished manually or by machine. By way of illustration and not limitation, stretching may be accomplished totally by hand using precut pieces or rolls of polymeric material, by clamping one end and pulling the other, by using at least one winding member and pulling one end of tubing manually in the opposite direction or using two winding members and mechanically running the second winding member at a higher speed than the first winding member, etc. Thus for instance if one desired a 200% draw down, the second winding member would run at twice the speed of the first, if an 800% draw down is desired, the second winding member wound run at 8 times the speed of the first winding member, etc.

As heretofore stated, the preferred microcatheter of this invention, made in the foregoing manner, are 28 gauge having an outer diameter of 0.368 mm and an inner diameter of 0.191 mm. These preferred microcatheters will have a tensile strength of at least 2.5 and preferably greater than 3.0 pounds. They may be prepared by elongating 200% a nylon tubing having an initial external diameter on the order of 0.737 mm, an internal diameter of on the order of 0.381 mm, and a breaking force of on the order of 3.5 pounds.

While 28 gauge microcatheters are preferred as heretofore noted the present invention contemplates preparing microcatheters from as small as 32 gauge (0.229 mm OD) to as large as 24 gauge (0.559 mm OD). The 32 gauge may be prepared by elongating a known 26 gauge nylon tubing having an OD of about 0.457 mm and a breaking force of on the order of 1.50 pounds to provide the 32 gauge microcatheter with a breaking force of on the order of 1.5 pounds. The 24 gauge may be prepared by elongating 200% a known 19 gauge nylon tubing having an OD of about 1.12 mm and a tensile strength of around 4.5 pounds to provide a 24 gauge microcatheter having a tensile strength of about 4.5 pounds.

Microcatheters of intermediate gauges from 25–27 gauge and from 29–31 gauge may be prepared in a similar manner.

The spinal needle through which the novel microcatheter is to be threaded, may be any of the ones heretofore known in the art having an external diameter from about 0.889 mm to about 0.457 mm, 0.711 mm being preferred; with an interior diameter from about 0.584 mm to about 0.254 mm, 0.406 mm being preferred. In use the particular internal diameter of the needle chosen will depend on the specific size microcatheter selected as the internal diameter of the needle will need to be sufficient to accommodate the microcatheter. The spinal needle most preferred for use with a 28 gauge microcatheter is commercially known as a 22 gauge and has a 0.711 mm external diameter and a 0.406 mm internal diameter. However, the selection of the particular spinal needle comprises no part of the present invention.

The following examples show by way of illustration and not limitation, the novel characteristics of the invention.

EXAMPLE I

Control

Twenty unstretched nylon 11 catheters having 300% elongation and an external diameter of 0.368 mm and an internal diameter of 0.191 mm and comprising 20% barium sulfate (for radiopacity) were subjected to tensile strength testing.

The results of these tests were as follows:

| Tensile Strength | Pounds Force |
| --- | --- |
| Minimum | 1.470 |
| Maximum | 1.910 |
| Average | 1.661 |
| Standard Deviation | 0.133 |

EXAMPLE II

Test

Fifty 22 gauge nylon 11 catheters with 20% barium sulfate capable of 300% elongation, and having an external diameter of 0.737 mm and an internal diameter of 0.381 mm were stretched 200% to a final external diameter of 0.368 mm and internal diameter of 0.191 mm, the dimensions of the 28 gauge catheters of Example 1. The resulting microcatheters were then subjected to breaking force testing.

The test results were as follows:

| Breaking Force | Pounds Force |
| --- | --- |
| Minimum | 2.945 |
| Maximum | 4.189 |
| Average | 3.612 |
| Standard Deviation | 0.261 |

The aforementioned data simply stated, illustrates an approximately 100% increase in breaking force by preparing the 28 gauge microcatheters by the novel process of this invention In the foregoing Examples, barium sulfate was added to the polymeric tubing to provide radiopacity for monitoring placement of the catheter by x-radiation. It will of course be appreciated that the present invention includes incorporating heavy metal salts such as barium sulfate for radiopacity as well as the other additives known in the catheter art imparting specified desired properties, e.g. bactericides and the like.

By way of recapitulation, in accordance with the present invention, microcatheters having appreciably increased tensile strength are obtained by subjecting catheter or other medical grade tubing to molecular orientation by stretching to reduce the OD or gauge to the desired size. The molecular orientation as a function of the elongation has been found to provide at least a 50% increase in tensile strength and, more typically, at least a 70% increase.

In the extrusion process to form the tubular article which can be said to be the starting point for the present invention, some degree of molecular orientation may occur. However, such molecular orientation is relatively insignificant, and in accordance with the present invention it is the further additional molecular orientation by elongation that is in fact the essence of this invention and the startling increase in tensile strength obtained thereby.

In view of the eventual use of the microcatheters in a sterile surgical environment, they may and typically will be packaged in sterile surgical kits and trays. Kits may comprise one or more spinal needles, syringes, filters, and adaptors or varying sizes. Surgical trays may comprise a prepping solution, drape(s), sponge(s), ephedrine, adaptor(s), catheter threading assisting device(s), catheter plug(s), syringe(s), filter(s), needle(s), anesthetic agent(s) and bandage(s).

Since certain changes may be made without departing from the scope of the invention herein involved, it is therefore intended that all matter described in the foregoing specification shall be interpreted as illustrative and not in a limiting sense.

I claim:

1. A microcatheter having a substantially improved tensile strength, mode from a method comprising the step of elongating and thereby molecularly orienting a medical grade tubular article having a greater gauge size than the microcatheter gauge size desired, thereby to reduce the gauge size to within the range of 24-32 gauge to form the microcatheter, the microcatheter having a breaking force substantially equal to that of the tubular article of greater size.

2. A microcatheter as defined in claim 1 wherein the tubular article is elongated at least 200 percent.

3. A microcatheter as defined in claim 1 wherein the tensile strength of the microcatheter is at least 50 percent greater than that of a microcatheter of the same gauge prepared by extrusion.

4. A microcatheter as defined in claim 1 wherein the microcatheter in claim 1 is of a size selected from the group consisting of 24, 28 and 32 gauge catheters.

5. A microcatheter as defined in claim 4 wherein the microcatheter is a 32 gauge catheter having a breaking force of at least about 1.5 pounds.

6. A microcatheter as defined in claim 4 wherein the microcatheter is a 28 gauge catheter having a breaking force of at least about 2.5 pounds.

7. A microcatheter as defined in claim 6 wherein the breaking force of the microcatheter is at least 3.0 pounds.

8. A microcatheter as defined in claim 4 wherein the microcatheter is a 24 gauge catheter and the breaking force is at least 4.5 pounds.

9. In a microcatheter comprising a flexible polymeric material;
the improvement wherein the polymeric material is molecularly oriented by stretching whereby to provide a microcatheter having an outside diameter within the range of 24-32 gauge and having greatly increased breaking force over that of a microcatheter of the same gauge which has not been molecular oriented by stretching.

10. A microcatheter as defined in claim 9 wherein the microcatheter is 28 gauge.

11. A microcatheter as defined in claim 10 wherein the breaking force is at least 2.5 pounds.

12. A microcatheter as defined in claim 11 wherein the polymeric material comprises nylon.

13. A microcatheter as defined in claim 9 wherein the microcatheter is a 24 gauge microcatheter.

14. A microcatheter as defined in claim 13 wherein the breaking force is at least 4.5 pounds.

15. A microcatheter as defined in claim 14 wherein the polymeric material comprises nylon.

16. A microcatheter as defined in claim 9 wherein the microcatheter is 32 gauge.

17. A microcatheter as defined in claim 16 wherein the breaking force is at least 1.5 pounds.

18. A microcatheter as defined in claim 17 wherein the polymeric material is nylon.

19. The process of administering continuous spinal anesthesia comprising the steps of inserting a microcatheter as defined in claim 9 through a spinal needle until the tip of the catheter projects beyond the tip of the spinal needle and enters the subarachnoid space, removing the spinal needle while maintaining the catheter in place, and administering the anesthetic agent.

* * * * *